US012419920B2

(12) United States Patent
Murphy et al.

(10) Patent No.: US 12,419,920 B2
(45) Date of Patent: *Sep. 23, 2025

(54) BIFIDOBACTERIUM LONGUM NCIMB 41676

(71) Applicant: PrecisionBiotics Group Limited, Cork (IE)

(72) Inventors: Eileen Frances Murphy, Cork (IE); Paul Enck, Berlin (DE); Christoph Braun, Tuebingen (DE); Huiying Wang, Shanghai (CN)

(73) Assignee: PrecisionBiotics Group Limited, Cork (IE)

( * ) Notice: Subject to any disclaimer, the term of this patent is extended or adjusted under 35 U.S.C. 154(b) by 111 days.

This patent is subject to a terminal disclaimer.

(21) Appl. No.: 18/455,329

(22) Filed: Aug. 24, 2023

(65) Prior Publication Data

US 2023/0414681 A1 Dec. 28, 2023

Related U.S. Application Data

(63) Continuation of application No. 16/767,874, filed as application No. PCT/EP2019/052138 on Jan. 29, 2019, now Pat. No. 11,771,723.

(30) Foreign Application Priority Data

Jan. 29, 2018 (EP) .................................... 18153993

(51) Int. Cl.
| | | |
|---|---|---|
| *A61K 35/745* | (2015.01) | |
| *A23L 33/135* | (2016.01) | |
| *A23L 33/21* | (2016.01) | |
| *A61K 9/00* | (2006.01) | |
| *A61K 9/14* | (2006.01) | |
| *A61K 9/20* | (2006.01) | |
| *A61K 9/48* | (2006.01) | |
| *A61K 39/39* | (2006.01) | |

(52) U.S. Cl.
CPC .......... *A61K 35/745* (2013.01); *A23L 33/135* (2016.08); *A23L 33/21* (2016.08); *A61K 39/39* (2013.01); *A61K 9/0053* (2013.01); *A61K 9/14* (2013.01); *A61K 9/20* (2013.01); *A61K 9/48* (2013.01)

(58) Field of Classification Search
CPC .................................................. A61K 35/745
See application file for complete search history.

(56) References Cited

U.S. PATENT DOCUMENTS

| | | | |
|---|---|---|---|
| 10,144,978 B2 | 12/2018 | O'Mahony et al. | |
| 10,813,366 B2 | 10/2020 | Murphy et al. | |
| 11,225,641 B2 | 1/2022 | O'Mahony et al. | |
| 11,771,723 B2 * | 10/2023 | Murphy ................ | A23L 33/135 424/93.4 |
| 2012/0276143 A1 | 11/2012 | O'Mahony et al. | |
| 2018/0282825 A1 | 10/2018 | O'Mahony et al. | |
| 2020/0289587 A1 | 9/2020 | Kiely et al. | |
| 2020/0289588 A1 | 9/2020 | Murphy et al. | |
| 2020/0325548 A1 | 10/2020 | O'Mahony et al. | |
| 2020/0375204 A1 | 12/2020 | Murphy et al. | |
| 2021/0127695 A1 | 5/2021 | Murphy et al. | |

FOREIGN PATENT DOCUMENTS

| | | |
|---|---|---|
| CN | 102206599 A | 10/2011 |
| EP | 1743633 A1 | 1/2007 |
| EP | 2438821 A1 | 4/2012 |
| JP | 2007169200 A | 5/2007 |
| JP | 2017081853 A | 5/2017 |
| WO | 2010/055499 A2 | 5/2010 |
| WO | 2010/055499 A3 | 5/2010 |
| WO | 2010/060722 A1 | 6/2010 |
| WO | 2011005853 A2 | 1/2011 |
| WO | 2011/058535 A1 | 5/2011 |
| WO | 2013/074531 A1 | 5/2013 |
| WO | 2015/146844 A1 | 1/2015 |
| WO | 2018/002238 A1 | 1/2018 |
| WO | 2018/002240 A1 | 1/2018 |

OTHER PUBLICATIONS

Allen, A.P. et al., "Bifidobacterium Longum 1714 as a Translational Psychobiotic: Modulation of Stress, Electrophysiology and Neurocognition in Healthy Volunteers", Translational Psychiatry, 6, e939 (2016).
Allen, A.P. et al., "Bifidobacterium Longum 1714: A Psychobiotic That Modulates Brian Activity, The Stress Response and Neurocognitive Performance in Healthy Volunteers", (2015).
Bravo, J.A. et al., "Ingestion of Lactobacillus Strain Regulates Emotional Behavior and Central GABA Receptor Expression in a Mouse Via the Vagus Nerve", PNAS, vol. 108, No. 38, pp. 16050-16055, (2011).
Burnet, P.W.J., et al., "Psychobiotics Highlight The Pathways to Happiness", Biological Psychiatry, vol. 74, No. 10, pp. 708-709 (2013).
Buysse, D.J., et al., "Quantification Of Subjective Sleep Quality in Healthy Elderly Men and Women Using The Pittsburgh Sleep Quality Index (PSQI)", Sleep, 14 (4): pp. 331-338, (1991).
Buysse, D.J., et al., "The Pittsburgh Sleep Quality Index: A New Instrument for Psychiatric Practice aAnd Research", Psychiatry Research, 28, pp. 193-213, (1988).
Colten, H.R., et al., "Sleep Disorders and Sleep Deprivation: An Unmet Public Health Problem", The National Academies Press, (2006).
Dinan, T.G., et al., "Psychobiotics: A Novel Class of Psychotropic", Science Diet, Biological Psychiatry, vol. 74, Issue 10, pp. 720-726, (2013).

(Continued)

*Primary Examiner* — Brian Gangle
*Assistant Examiner* — Lakia J Jackson-Tongue
(74) *Attorney, Agent, or Firm* — Bookoff McAndrews, PLLC

(57) ABSTRACT

*Bifidobacterium longum* strain NCIMB 41676 is useful for improving or sustaining vitality and/or reducing mental fatigue in stressful situations.

20 Claims, 8 Drawing Sheets

(56) References Cited

OTHER PUBLICATIONS

Fillingim, R.B., et al., "Potential Psychosocial Risk Factors For Chronic TMD: Descriptive Data and Empirically Identified Domains From The OPPERA Case-Control Study", Journal Pain, (2012).
Herman, C.R., et al., "The Effectiveness of Adding Pharmacologic Treatment With Clonazepam oOr Cyclobenzaprine to Patient Education and Self-Care for the Treatment of Jaw Pain Upon Awakening: a Randomized Clinical Trial", Journal Orofac Pain, 16(1) pp. 64-70, Winter (2002).
Health and Nutritional Properties of Probiotics in Food Including Powder Milk With Live Lactic Acid Bacteria, (2001).
International Search Report for PCT/EP2019/052138 dated Apr. 17, 2019 (3 pages).
Jay et al., "Modern Food Microbiology", 7th edition, (2005).
Kazemi, A. et al., "Effect of Probiotic and PreBiotic vs Placebo on Psychological Outcomes in Patients With Major Depressive Disorder: a Randomized Clinical Trial", Clinical Nutrition, (2018), https://doi.org/10.1016/j.clnu.2018.04.010.
Kell, Douglas B. et al., "Viability and Activity in Readily Culturable Bacteria: a Review and Discussion of the Practical Issues", https://link.springer.com/article/10.1023/A:1000664013047.
Mairesse, J. et al., "Lactobacillus Reuteri DSM 17938 and Bifidobacterium Longum Atcc BAA-999 Normalize Sleep Patterns in Prenatal Stress Rats", Human Physiology and Pharmacology, University of Rome, p. 797 (2011).
Parmar, Arpit, "Gut-Brains Axis, Psychobiotics, and Mental Health", Asian Journal of Psychiatry, Elsevier, Amsterdam, NL, vol. 22, pp. 84-85 (2016).
Pinto-Sanchez, Maria Ines et al., "Probiotic Bifidobacterium Longum NCC3001 Reduces Depression Scores and Alters Brain Activity: a Pilot Study in Patients With Irritable Bowel Syndrome", Gastroenterology, (2017).
Porto, Felipe et al., "Differences in Psychosocial Functioning and Sleep Quality Between Idiopathic Continuous Orofacial Neuropathic Pain Patients and Chronic Masticatory Muscle Pain Patients", Journal of Orofacial Pain, vol. 25 Issue 2, pp. 117-124 (2011).
Savignac, H.M. et al., "Bifidobacteria Exert Strain-Specific Effects on Stress-Related Behavior and Physiology in BALB/c Mice", Neurogastroenterology & Motility, 26, pp. 1615-1627 (2014).
Savignac, H.M. et al., Bifidobacteria Modulate Cognitive Processes in an Anxious Mouse Strain, Behavioural Brain Research, 287, pp. 59-72 (2015).
U.S. Appl. No. 16/789,768, filed Feb. 13, 2020.
U.S. Appl. No. 16/767,836, filed May 28, 2020.
Wang, "Effects of Probiotics on Central Nervous System Functions in Humans", pp. 1-152 (2017).
Pinto-Sanchez, Maria I., et al., "Probiotic Bifidobacterium longum NCC3001 Reduces Depression Scores and Alters Brain Activity: A Pilot Study in Patients With Irritable Bowel Syndrome", Gastroenterology, vol. 153, pp. 448-459 (2017).
Brooks, M., "'Psychobiotic' May Help Erase Stress, Improve Memory", www.medspace.com, pp. 1-2 (Oct. 2015).
Torday et al., EMBO Rep., 2019; 20(1) (2019).
https://www.nia.nih.gov/health/what-are-signs-alzheimers-disease#:-: text=For%20most%20people%20with%20Alzheimer's,vary% 20from%20person%20to%20person (Year: 2022).
Ware Jr. et al., Med Care., 1992, 30(6):473-83 (1992).
Physiopedia, https://www.physio-pedia.com/36-Item_Short_Form_Survey_(SF-36), accessed May 25, 2022 (2022).
Singh, Ann Indian Acad Neurol 2014:17 (Supplement 1):S107-12 (2014).
Dr. Amy Meyers (section 5. Relieve Stress)—7 Ways to Improve memory and Focus at Any Age; https://www.amymyersmd.com/article/improve-memory-focus/; accessed May 25, 2022. (2022).
Lins et al., SAGE Open Medicine, 2016; 4: 1-12 (2016).
Wang, Neurogastroenterology and motility, 2018; 30(1) (abstract 024) (2018).
Healthline, https://www.healthline.com/health/mental-exhaustion, accessed on Oct. 6, 2021 (2021).
Rao et al., "A randomized, double-blind, placebo-controlled pilot study of a probiotic in emotional symptoms of chronic fatigue syndrome", Gut Pathogens, vol. 1, No. 6, 6 pages, Mar. 19, 2009.
Steenbergen, Laura, "A randomized controlled trial to test the effect of multispecies probiotics on cognitive reactivity to sad mood", Brain, Behavior, an Immunity, vol. 28, pp. 258-264, Aug. 2015.
Romjin et al., "Systematic review of evidence to support the theory of psychobiotics", Nutrition Reviews, vol. 73, No. 10, pp. 675-693, Sep. 14, 2015.
Kroenke et al. "The Patient Health Questionnaire Somatic, Anxiety, and Depressive Symptom Scales: a systematic review", General Hospital Psychiatry, vol. 23, No. 4, pp. 345-359, Jul.-Aug. 2010.
Longstreth et al., "Functional Bowel Disorders", Gastroenterology, vol. 130, No. 5, pp. 1480-1491, Apr. 2006.

\* cited by examiner

BIFIDOBACTERIUM LONGUM NCIMB 41676

CROSS-REFERENCE TO RELATED APPLICATIONS

This application is a continuation of U.S. application Ser. No. 16/767,874, filed on May 28, 2020, which is the U.S. national phase entry under 35 U.S.C. § 371 of International Application No. PCT/EP2019/052138, filed on Jan. 29, 2019, incorporated by reference herein in its entirety, PCT/EP2019/052138 claiming the benefit of priority to European Application No. 18153993.3 filed on Jan. 29, 2018.

INTRODUCTION

The largest population of microorganisms on the human body resides in the gastrointestinal tract. Known as the gut microbiota, this complex ecosystem is comprised of microorganisms including bacteria, fungi and archaea from over 60 genera. In terms of genes we are more that 99% microbial. Gradually we have come to realise that the microbiome plays a role in programming all the major body systems, including the brain. However we are only at the beginning of understanding this highly complex bi-directional system.

Probiotics are defined as live bacteria, which when ingested in adequate amounts, confer a health benefit (WHO, 2001). Recent evidence suggests that probiotics may have a role to play in mental health and well-being (1).

WO2011/058535A described *Bifidobacterium longum* strain NCIMB 41676 (1714™ strain). Feeding of mice with the NCIMB 41676 strain was associated with increased IL-10 and decreased TNF-α, INF-γ and IL-12 in healthy animals in a model of sepsis/inflammation.

NCIMB 41676 also had immunomodulatory activity when co-incubated with human immune system cells in-vitro. NCIMB 41676 reduced LPD-induced NFkB activity in an in-vivo murine sepsis/inflammation model. It was hypothesised that this anti-inflammatory effect might also have effects modulated through the gut-brain axis and would therefore be a candidate for research in this area. It was shown that, in mice, the strain exhibited positive benefits in mice in tail suspension, fear conditioning and marble burying tests.

Savignac et al., Neurogastroenterol Motil (2014) 26, 1615-1627, reported that certain bifidobacteria exert strain-specific effects on stress-related behaviour and physiology in BALB/c mice. *Bifidobacterium longum* NCIMB 41676 (1714™), *B. breve* 1205 and the antidepressant escitalopram reduced anxiety in the marble burying test. 1714 decreased stress-induced hyperthermia and induced antidepressant-like behaviour in the tail suspension test. However, there was no difference in corticosterone levels between the groups of mice. Savignac et al., Behavioural Brain Research 287 (2015) 59-72, assessed the effect of feeding BALB/c mice with *Bifidobacterium longum* NCIMB 41676 and *B. breve* 1205. In an object recognition test, *B. longum* NCIMB 41676 fed mice discriminated between two objects faster than *B. breve* 1205 fed mice. In a Barnes maze test, *B. longum* NCIMB 41676 fed mice made fewer errors than *B. breve* 1205 fed mice. In a fear conditioning test, *B. longum* NCIMB 41676 treated mice showed better learning and memory, yet presenting the same extinction learning profile as controls.

Allen et al 2016 assessed the effect of feeding healthy human adults with *B. longum* NCIMB 41676. Attenuated responses to psychological and physiological stress and modest improvement over placebo in cognitive performance are reported.

Quality of life (QOL) is defined as the general well-being of individuals and societies. Within clinical research, it can take account of the physical but also the mental well-being and can be measured using validated (QOL) tools in clinical research. Mental well-being is often impaired in everyday life due to busy lifestyle habits including insufficient rest and sleep, irregular meal patterns, and lack of exercise. One can recover by rest and relaxation; however, when the decline in mental health and well-being becomes advanced or prolonged, it can result in problems such as reduced ability to cope with everyday stress, mental fatigue and may impair mental performance. Therefore, maintaining positive mental well-being and vitality is very important.

There have been some translational studies in healthy volunteers, psychiatric patients, and patients with irritable bowel syndrome with anxiety and depression (2-5). To date none of the studies that have assessed the effect of a probiotic on the CNS have shown an effect on quality of life measurements.

STATEMENTS OF INVENTION

According to the invention there is provided *Bifidobacterium longum* strain NCIMB 41676 for use in improving or sustaining vitality and/or reducing mental fatigue in mammals.

The invention also provides *Bifidobacterium longum* strain NCIMB 41676 for use in improving or sustaining vitality and/or reducing mental fatigue in humans.

The invention also provides *Bifidobacterium longum* strain NCIMB 41676 for use in counter-regulating stress responses and/or negative emotions in humans. The negative emotion may be caused by social stress.

Also provided is *Bifidobacterium longum* strain NCIMB 41676 for use in counter-regulating social stress in humans.

In one aspect the invention provides *Bifidobacterium longum* strain NCIMB 41676 for use in counter-regulating social rejection/ostracism in humans The invention also provides *Bifidobacterium longum* strain NCIMB 41676 for use in for improving coping skills in stressful situations in mammals.

Also provided is *Bifidobacterium longum* strain NCIMB 41676 for use in for improving coping skills in stressful situations in humans.

The *Bifidobacterium* strain NCTMB 41676 may be in the form of viable cells.

The *Bifidobacterium* strain NCIMB 41676 may be in the form of non-viable cells.

The *Bifidobacterium* strain NCIMB 41676 may be present in the formulation in an amount of more than $10^6$ cfu, typically from $10^7$ to $10^{10}$, typically from $10^8$ to $10^9$ cfu. In one case the *Bifidobacterium* strain NCIMB 41676 is present in the formulation in an amount of about $1 \times 10^9$ cfu.

Bacterial viability reflects the number of culturable bacteria within a sample, i.e. the number of bacteria which retain the ability to reproduce when grown under optimal conditions (Viable cells). Put another way viability reflects the number of individual bacterial cells which retain the 25 ability to replicate into larger bacterial colonies (colony forming units (CFUs)).

Viability is commonly determined using plate-counting methods, whereby a bacterial sample is diluted and then incubated on an agar plate containing the necessary nutrients for growth. Viability is then calculated from the number of bacterial colonies identified on a plate. Such methods are summarized in Modern Food Biology 2005 7th edition, James Monroe Jay, Martin J. Loessner, David A. Golden, Springer Science, New York.

Whilst plate-counting gives a good indication of viability, it does not encompass all living bacterial cells in the sample. (Kell, Douglas B., et al. "Viability and activity in readily culturable bacteria: a review and discussion of the practical issues." *Antonie van Leeuwenhoek* 73.2 (1998): 169-187).

Samples will also contain "viable but non-culturable" (VBNC) cells which remain metabolically active but have lost the ability to replicate at the time of analysis by plate count, and thus despite being alive will not form CFUs. Finally, samples will also contain dead cells. These two groups can be grouped together as "Non-Viable cells". Therefore Non-viable cells are the inverse of Viable cells i.e. all those cells which have lost the ability to replicate when tested.

All samples containing Viable cells will also contain Non-Viable cells, therefore the definition of a Viable cell culture is clarified using CFU measurements.

All Non-Viable samples will contain at least VNBCs and possibly small amounts of Viable cells. Industry standard lower level detection limits of $10^3$ CFU/g viable cells allow for the inherent process variability caused by the presence of a certain number of VBNCs/Viable cells in Non-Viable samples.

In some embodiments, such as, but not limited to, special sterile food products or medicaments a non-replicating form of a probiotic strain may be preferable. For example, at least 95%, preferably at least 97%, more preferably at least 99% of the Bifidobacteria strain can be non-replicating in the composition.

In some embodiments the formulation is in the form of a bacterial broth.

In some cases the formulation in the form of a freeze dried powder.

The formulation may further comprise a prebiotic material.

In some cases the formulation further comprises an ingestible carrier. The ingestible carrier may be a pharmaceutically acceptable carrier such as a capsule, tablet or powder. Alternatively, the ingestible carrier is a food product such as acidified milk, yoghurt, frozen yoghurt, milk powder, milk concentrate, cheese spreads, ice cream, dressings or beverages.

In some embodiments the formulation is in the form of a fermented food product.

The formulation may be in the form of a fermented milk product.

In some cases the carrier does not occur in nature.

The formulation may further comprise a protein and/or peptide, in particular proteins and/or peptides that are rich in glutamine/glutamate, a lipid, a carbohydrate, a vitamin, mineral and/or trace element.

The formulation may further comprise an adjuvant.

The formulation may further comprise a bacterial component.

The formulation may further comprise a drug entity.

The formulation may further comprise a biological compound.

The strains are in the form of freeze dried powder which is blended with food grade excipient, and filled into a format such as a sachet or capsule.

The strain of the invention may be administered to animals (including humans) in an orally ingestible form in a conventional preparation such as capsules, microcapsules, tablets, granules, powder, troches, pills, suppositories, suspensions and syrups. Suitable formulations may be prepared by methods commonly employed using conventional organic and inorganic additives. The amount of active ingredient in the medical composition may be at a level that will exercise the desired therapeutic effect.

The formulation may also include a drug entity or a biological compound.

In addition a vaccine comprising the strains of the invention may be prepared using any suitable known method and may include a pharmaceutically acceptable carrier or adjuvant.

The introduction of probiotic organisms is accomplished by the ingestion of the micro-organism in a suitable carrier. It would be advantageous to provide a medium that would promote the growth of these probiotic strains in the large bowel. The addition of one or more oligosaccharides, polysaccharides, or other prebiotics enhances the growth of lactic acid bacteria in the gastrointestinal tract. Prebiotics refers to any non-viable food component that is specifically fermented in the colon by indigenous bacteria thought to be of positive value, e.g. bifidobacteria, lactobacilli. Types of prebiotics may include those that contain fructose, xylose, soya, galactose, glucose and mannose. The combined administration of a probiotic strain with one or more prebiotic compounds may enhance the growth of the administered probiotic in vivo resulting in a more pronounced health benefit, and is termed synbiotic.

It will be appreciated that the probiotic strains may be administered prophylactically or as a method of treatment either on their own or with other probiotic and/or prebiotic materials as described above. In addition, the bacteria may be used as part of a prophylactic or treatment regime using other active materials such as those used for treating related conditions especially those with an immunological involvement. Such combinations may be administered in a single formulation or as separate formulations administered at the same or different times and using the same or different routes of administration.

The strains of the invention may be formulated to facilitate controlled release such as a delayed release of the strain. For example, the formulation may be adapted to release the strain at a particular location in the gastrointestinal tract such as the small intestine or in the colon. To achieve such a controlled release the strain may be formulated in a capsule which has a coating which is adapted to release the strain at a particular location. A range of coatings are available to facilitate such controlled release. One such family of coatings are those available under the Trade Mark Eudragit.

A projected doubling in the global population of people aged ≥60 y by the year 2050 has major health and economic implications, especially in developing regions. Burdens of unhealthy aging associated with chronic noncommunicable and other age-related diseases may be largely preventable with lifestyle modification, including diet. However, as adults age they become at risk of "nutritional frailty," which can compromise their ability to meet nutritional requirements at a time when specific nutrient needs may be high. Ageing is a complex phenomena with multiple feedback loops between mental frailty and physical frailty, exercise, nutrition and an individuals microbiome. Mental resilience can be seen as a trait that enables an individual to recover from stress and to face the next stressor with optimism. People with resilient traits are considered to have a better mental and physical health. Early research indicates that mental resilience was significantly correlated with perceived health and perceived immune functioning (Van Schrojenstein et al., 2017). The ability to impact mental resilience and vitality in the elderly through the use of an easily administered probiotic would provide a new approach to help combat the effects of aging.

In some cases the formulation may be suitable for ingestion by a companion animal such as a dog or a cat. One such formulation is a dry pet food which may include any one or more of a carbohydrate source, a protein source and a lipid source.

BRIEF DESCRIPTION OF THE DRAWINGS

The invention will be more clearly understood from the following description thereof, given by way of example only, in which:—

DETAILED DESCRIPTION

A deposit of *B. longum* 1714™ strain was made at the National Collections of Industrial and Marine Bacteria Limited (NCIMB) Ferguson Building, Craibstone Estate, Bucksburn, Aberdeen, AB21 9YA, Scotland, UK on Nov. 5, 2009 and accorded the accession number NCIMB 41676.

WO2011/05853A, the entire contents of which are incorporated herein by reference, describes *B. longum* 1714™ strain—NCIMB 41676.

In a randomized, double-blinded, placebo-controlled trial, the effects of *B. longum* 1714™ strain was studied in comparison to placebo on 1) brain activity and quality of life measures in healthy subjects and 2) brain activity and coping skills and mental well-being associated with an induced social stressor. Forty-three healthy volunteers received either *B. longum* 1714™ or placebo for four weeks. Their health status was assessed using the 36-item short-form health survey (SF36) quality of life tool, and brain activation was studied before and after the application of a social stress test using magnetoencephalography (MEG). The 36-item short-form health survey (SF36) is a highly validated quality of life (QOL) tool to understand vitality, physical, social, emotional and mental functioning. Specifically, the SF36 includes eight subscales: physical functioning, bodily pain, role limitations due to physical health problems, role limitations due to personal or emotional problems, emotional well-being, social functioning, energy/vitality, and general health perceptions. Magnetoencephalography (MEG) is a functional neuroimaging technique for mapping brain activity by recording magnetic fields produced by electrical currents occurring naturally in the brain using very sensitive magnetic techniques. *B. longum* 1714™ strain was selected as it had previously been demonstrated to modulate stress related behaviours in animals (8, 9). Supporting evidence is also provided by a clinical study that showed reduced stress responses in response to an acute physical test—the cold pressor test and improved cognitive activity following treatment (10). However, the cold pressor test which is a physical induced stressor is different to a social exclusion test which is an emotional challenge. The cold pressor test is a cardiovascular test performed by immersing the hand into an ice water container, usually for one minute, and measuring changes in blood pressure and heart rate as well as cortisol responses. These changes relate to acute vascular and pulse excitability. Other measures can also be obtained from the cold pressor such as pain threshold and pain tolerances. In fact, a social stress induces an emotional response but not a change in blood pressure, heart rate or cortisol response.

Figure 2:
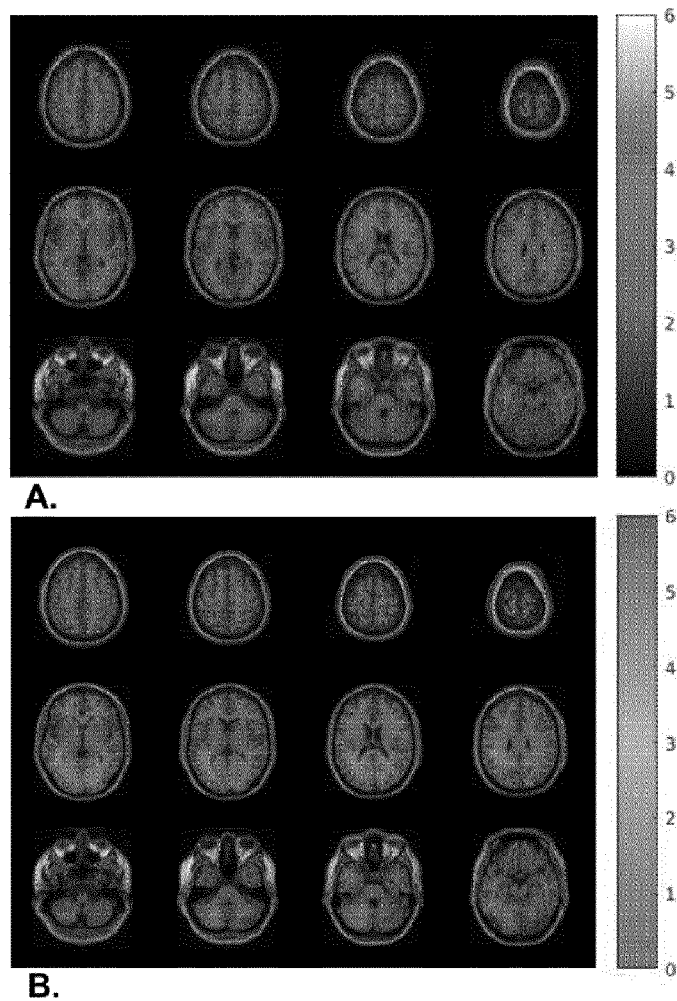
FIG. 2 are images that illustrate the difference of neural activity change during resting-state comparing *B. longum* 1714 vs. placebo. A. After the intervention, an increased theta band (6 Hz) power was obtained in a cluster including regions of bilateral IFC, MFC, and the bilateral ACC and MCC, comparing *B. longum* 1714 with the placebo group (p<0.05). B. After the intervention, reduced beta-2 band (26 Hz) power was obtained in a cluster, consisting of the bilateral FFG and HIPP, left ITC and STC, bilateral MTC and left CBL, comparing *B. longum* 1714 with the placebo group (p<0.05)
Figure 3:
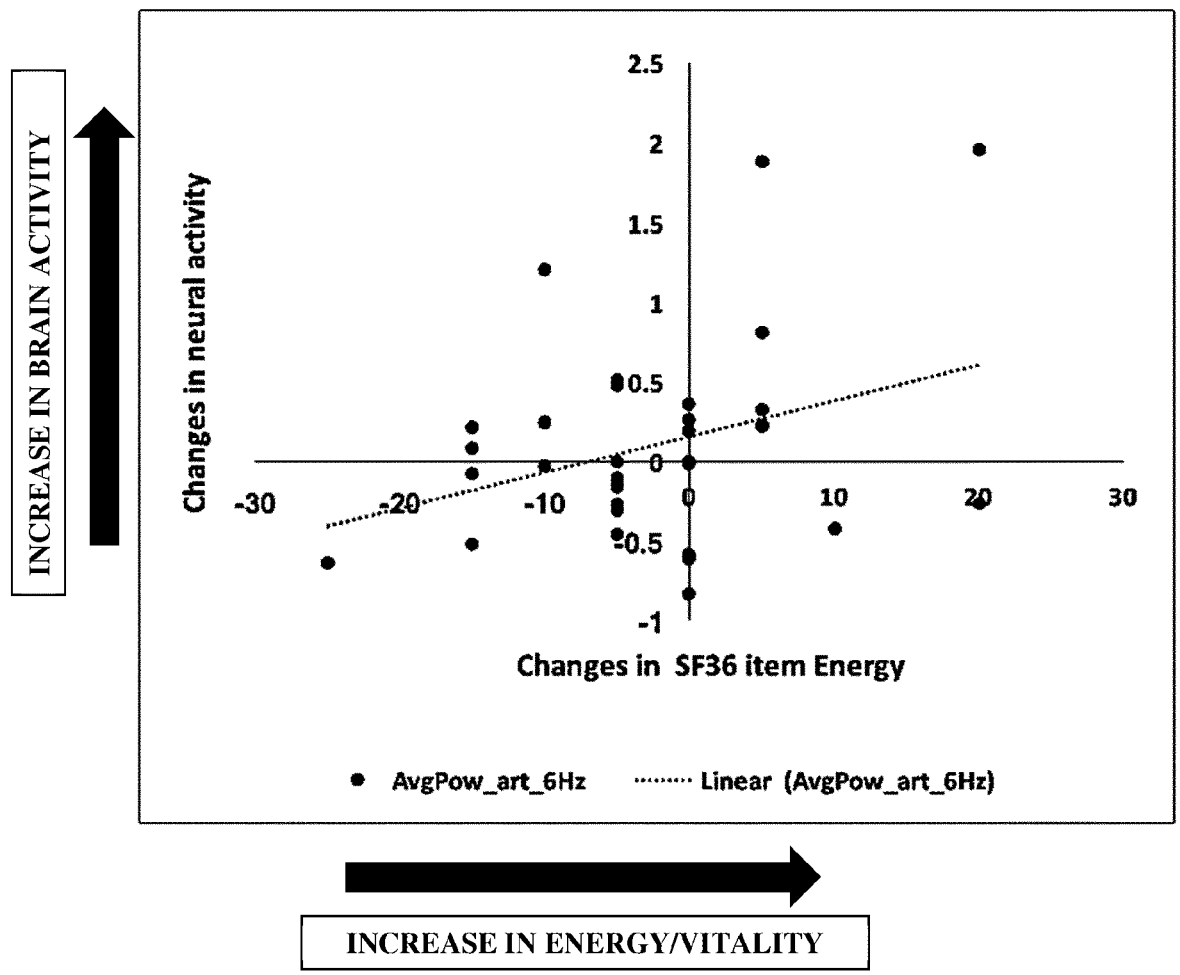
FIG. 3 is a chart of the correlation between neural activity change and SF36 change. In all groups, a positive correlation was obtained between changes of SF36 item "Energy/Vitality" with changes of theta band power in the cluster (r=0.33, p=0.04). In only *B. longum* 1714™ group, changes of SF36 item 'Energy/Vitality' positively correlated with change of averaged theta band power (r=0.61, p=0.007), and negatively correlated with change of beta-3 band power in the activated clusters during the resting state, respectively (r=−0.50, p=0.04)

Example 1—the Effects of *B. longum* 1714™ Strain in Comparison to Placebo on Brain Activity and Quality of Life Measures in Healthy Subjects Prior to any Induced Stressor being Applied Compared to placebo the *B. longum* 1714™ strain was effective in altering brain activity at particular wavelengths in certain regions of the brain (FIG. 2). Specifically, the *B. longum* 1714™ affected resting state brain oscillations with an increase in theta band in the frontal and cingulate cortex (p<0.05) and a decrease in beta-3 band in the hippocampus, fusiform, and temporal cortex (p<0.05). These areas represent important regions of the brain which are critical to human emotions, learning and memory functions. Correlation analysis showed that there were no correlations between these changes in brain activity and any SP36 parameter in the placebo fed group whereas surprisingly there were significant correlations between change in brain activity and SF36 sub-scale vitality scores in the *B. longum* 1714™ fed subjects (FIG. 3 and Table 3). This has never been seen before. Vitality questions included: 'Did you feel full of pep?', 'Did you have a lot of energy?', 'Did you feel worn out?', 'Did you feel tired?

These results indicate that *B. longum* 1714™ affects brain activity in healthy subjects in important regions of the brain which are related to increased vitality and reduced mental fatigue.

TABLE 1

Correlations between brain activity and Energy Vitality Measurements

| Groups | Sub-jective item | Resting state MEG | | Functional MEG during Cyberball | |
|---|---|---|---|---|---|
| | | Theta band power change | Beta-3 band power change | Theta band power change | Alpha band power change |
| *B. longum* group | SF36-Energy/Vitality | r = 0.61 p = 0.007 | r = −0.50 p = 0.04 | — | — |

Abbreviations: SF36, 36-item short-form health survey; NTS, Need Threat Scale; MEG, magnetoencephalography.

Example 2—Effects of *B. longum* 1714™ on Brain Activity and Coping Skills and Mental Well-being Associated with an Induced Social Stressor Numerous studies have utilized a standardized paradigm, called the "Cyberball Game", to study the effects of social stress and ostracism (exclusion), and the corresponding responses in the brain (11). However, this is the first study to test the effect of a probiotic on social stress and ostracism in humans.

The Cyberball Game is "an online ball-tossing game that participants believe they are playing with two or three players" (11). In the Cyberball Game, the participants are asked to play a ball tossing game with two other virtual players programmed by the experimenter using an on-line game. They were made believe that the two players were real and were playing the game.

Figure 4:
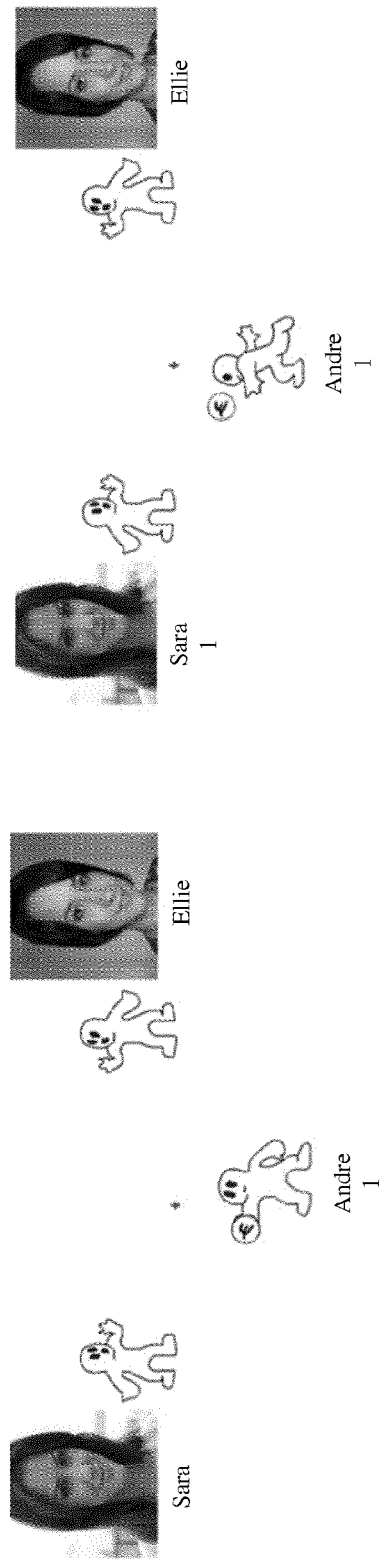
FIG. 4 is a schematic outline of a trial in a Cyberball game.

During the game, the participant is included in tossing the ball to each other and then excluded from the game (see FIG. 4). Participants complete three questionnaires to assess their level of distress, coping and mental well-being during exclusion from the game and inclusion. The questionnaires used included Need Threat Scale, the Mood Questionnaire and the Subjective 'Exclusion Perception'); all these scales are validated standards for the Cyberball Game (11). The Need Threat Scale was designed to measure the feelings and emotional consequences of social rejection, and higher scores related to higher distress level. Its four items (rated between 1 and 5 for "weak" to "strong") comprised self-esteem, belonging, meaningful existence and control, and combined ratings have been used as a measure of social distress in previous studies. The Mood Questionnaire was used to assess mood, using 8 questions (are you feeling bad, good, happy, sad, pleasant, angry, friendly and unfriendly), all rated between 1 and 5. The Subjective 'Exclusion Perception was to record participants' feeling of being included/ostracized by asking them to rate two statements ('I was ignored' and 'I was excluded') between 1 and 5. In general, with this game, participants feel more distressed in periods when they are excluded from the game compared to the periods in which they are included in the game Indeed, social stress during the Cyberball Game was consistently associated with altered brain activity in certain brain areas involved in emotions, (12).

Figure 5:
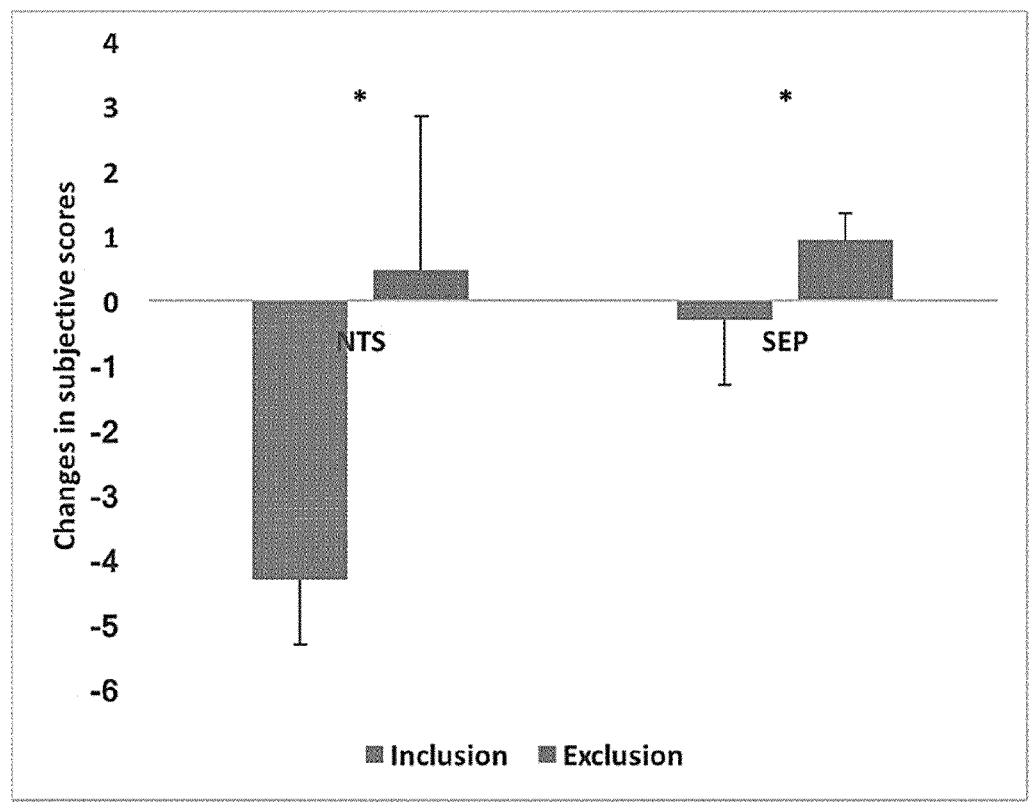
FIG. 5 is a bar chart of the main effects of condition on the Need Threat Scale (NTS) and the 'Exclusion Perception' (SEP). Participants in all groups reported increased scores of NTS and SEP in the exclusion condition compared to inclusion condition, after 4 weeks' intervention; inferior, middle and superior frontal cortex (IFC, MFC and SFC), and the bilateral anterior and middle cingulate cortex (ACC and MCC)

In this study, the Cyberball Game resulted in increased distress after 4-weeks intervention in the healthy subjects as measured by the validated Need Threat Scale and Subjective 'Exclusion Perception' questionnaires (FIG. 5). This means that the model worked and when subjects were excluded from the game their mood worsened and their stress increased. When included in the game, they felt better.

Figure 6:
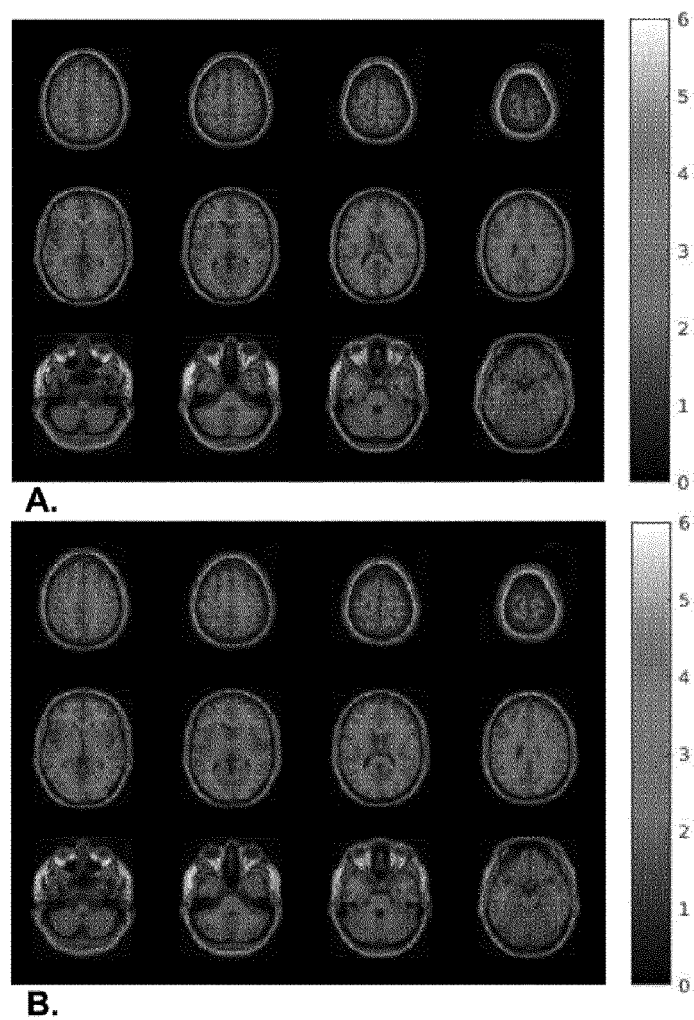
FIG. 6 are images that illustrate the difference of neural activity change during the CBG comparing *B. longum* 1714™ vs. placebo. A. Theta band showed an increased power in a cluster, consisting of the right inferior, middle and superior frontal cortex (IFC, MFC and SFC), the left bilateral anterior and middle cingulate cortex (ACC and MCC) and the right supramarginal gyrus (SMG), comparing *B. longum* 1714™ group and the placebo group in both conditions (p=0.03). B. Alpha band power also showed an increased power in cluster, including regions of the right IFC the bilateral MFC and SFC, the bilateral ACC and MCC, and the right SMG, comparing *B. longum* 1714™ group and the placebo group in both conditions (p=0.04). No main effect of condition or interaction of intervention and condition were observed.

Interestingly, the group that received *B. longum* 1714™ showed brain activity changes compared to placebo in response to the Cyberball game. Specifically, only in the *B. longum* 1714™ group and not in the placebo group, brain activity during the Cyberball game showed increases in theta and alpha bands power in the frontal and temporal cortex and supramarginal gyrus (p=0.03; 0.04) (FIG. 6).

Figure 7:
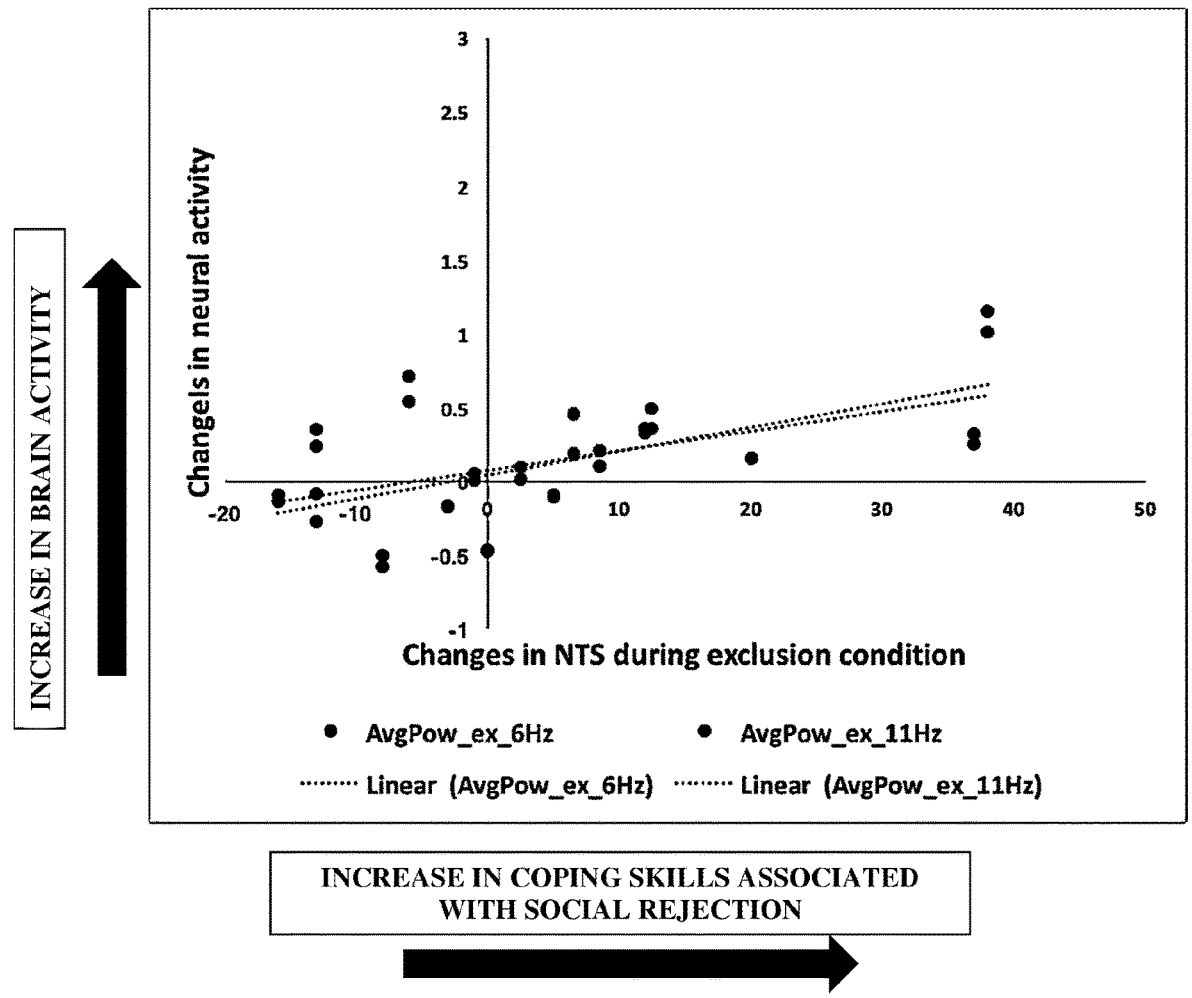
FIG. 7 is a chart of the correlation between neural activity change during the CBG and subjective score changes. Only in *B. longum* 1714™ group and only during the exclusion condition, NTS changes positively correlated with changes of the theta band power (r=0.62, p=0.008) and alpha band power (r=0.54, p=0.03)

Furthermore, in the *B. longum* 1714™ fed group that were left out of the game, correlation analysis shows that the more the change in brain activity the better they were able to cope compared to the placebo fed group, as measured by the Need Threat Scale, (FIG. 7). The Need Threat Scale is designed to measure the feelings and emotional consequences of social rejection, and higher scores related to higher distress level. Its four items (rated between 1 and 5 for "weak" to "strong") comprised self-esteem, belonging, meaningful existence and control, and combined ratings have been used as a measure of social distress in previous studies. Specifically, only with *B. longum* 1714™ and only during exclusion from the game was there a positive correlation with changes of the theta band power (r=0.62, p=0.008) and alpha band power (r=0.54, p=0.03;) with change in mental well-being (FIG. 7, Table 2). This shows that *B. longum* 1714™ affecting an individuals' neurophysiology in a way that may help in coping better with a social stress challenge. This is a novel finding in humans and was unexpected as emotional regulation is complex. It is surprising that a probiotic could impact such a complicated brain function in such a way.

TABLE 2

Correlations between brain activity and Social Ostracism/Rejection Measurements

| Groups | Sub-jective item | Resting state MEG | | Functional MEG during Cyberball | |
|---|---|---|---|---|---|
| | | Theta band power change | Beta-3 band power change | Theta band power change | Alpha band power change |
| *B. longum* group | Need Threat Scale | — | | r = 0.62 - p = 0.008 | r = 0.54 - p = 0.03 |

Abbreviations: NTS, Need Threat Scale; MEG, magnetoencephalography.

Example 3—Effect of *B. longum* 1714™ on Energy and Concentration in Healthy Humans An on-line study was performed with 42 healthy volunteers taking *B. longum* 1714™ for 5 weeks.

Participants were asked the following questions:
1. Reflecting over the last week how would you rate your Energy levels? (0=very low energy, 9=very high energy)
2. Reflecting over the last week how would you rate your ability to concentrate? (0=completely distracted, 9=excellent concentration)

Figure 8:
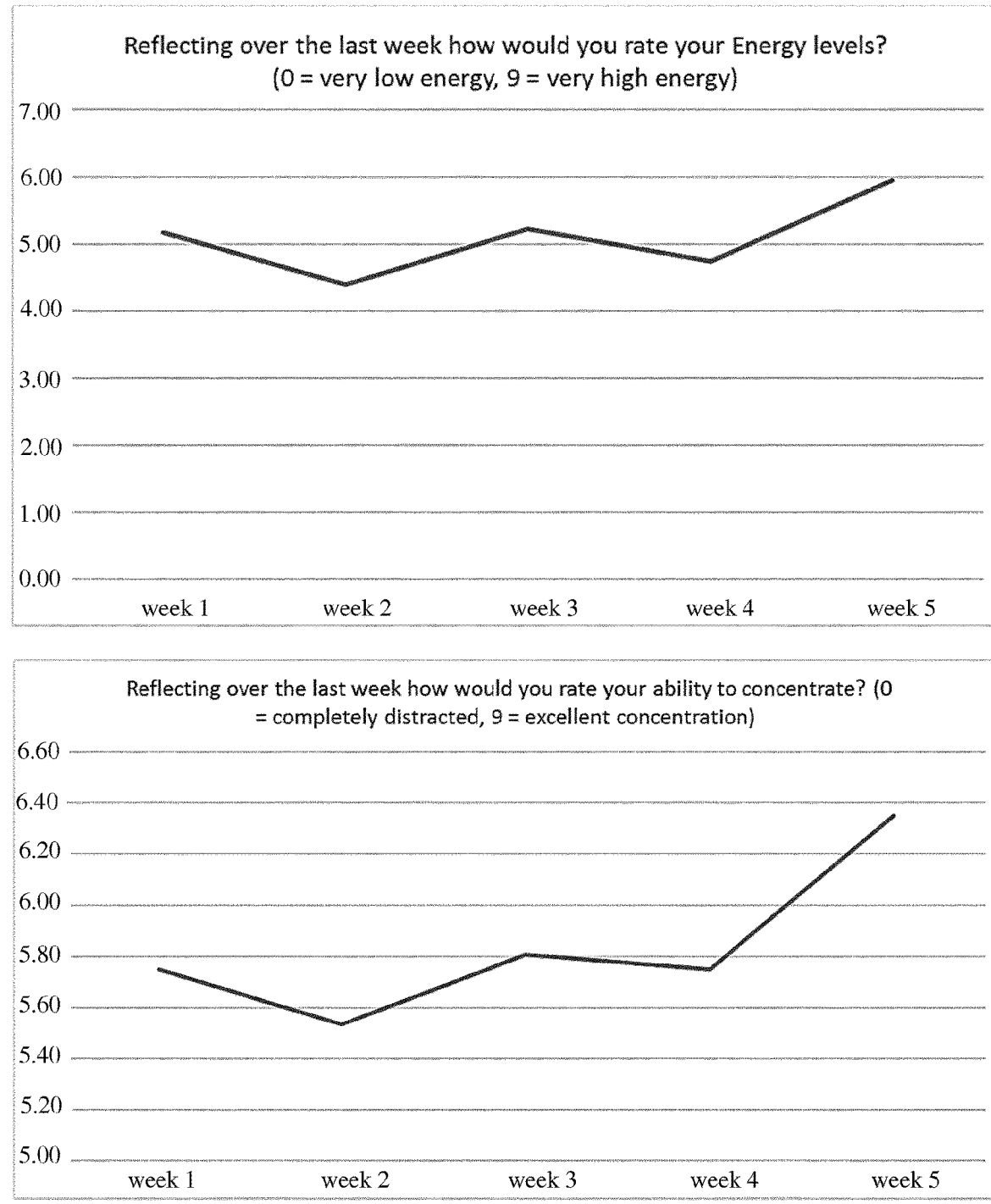
FIG. 8 are graphs illustrating the effect of *B. longum* 1714™ strain on energy/vitality, concentration and stress in an online study with healthy volunteers.

The results of this study showed that energy levels and ability to concentrate increased progressively over the course of the study (FIG. 8). This supports our work which shows that *B. longum* 1714™ increases vitality/energy and reduces mental fatigue.

2) Materials and Methods

The effects of *B. longum* 1714™ strain in comparison to placebo on brain activity and quality of life measures and mental well-being associated with an induced social stressor in healthy subjects.

2.1 Participants

Figure 1:
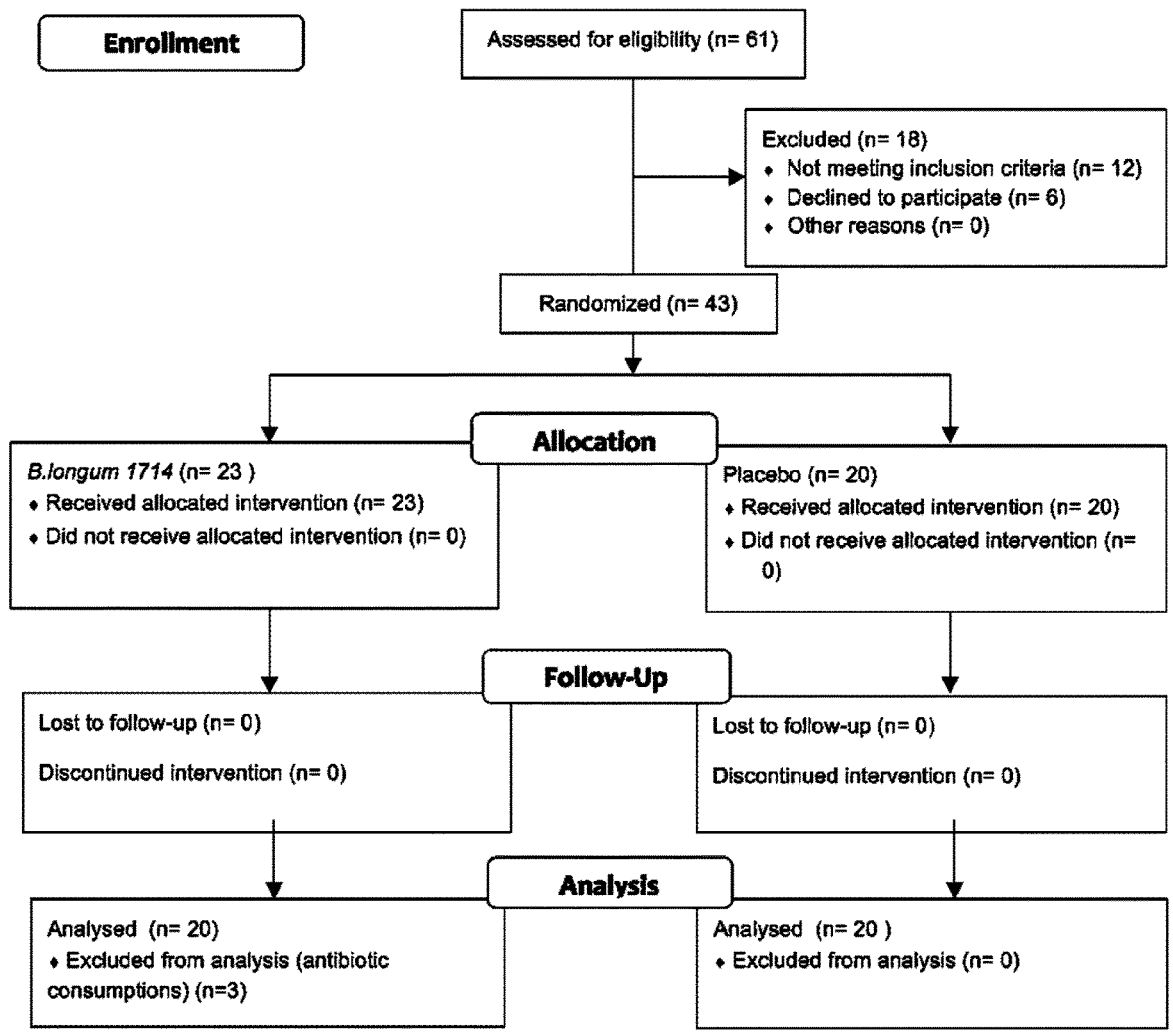
FIG. 1 is a CONSORT flow diagram of a clinical trial.

Based on previously published data (11), we estimated that—with a power of 0.95 for a 2×2 repeated measure ANOVA—a minimum sample size of 34 was required to demonstrate an effect size $f=0.2$ at $\alpha=0.05$ in a parallel-group designed study. The study was completed with 40 healthy volunteers, after having recruited initially sixty-one participants. Eighteen participants were excluded because they did not meet the inclusion criteria, and three of them could not be included in the final analysis because of the intake of an antibiotic during the intervention period (see FIG. 1 for detailed trial profile). Criteria for inclusion were: 1) non-smoker for at least 3 months, 2) a body mass index (BMI) of 18-30, 3) no chronic allergies, 4) willing to discontinue their normal consumption of probiotics and prebiotic-containing foods or potentially immune-enhancing dietary supplements, 5) receiving no immune-suppressing intervention and not having any immunosuppressive illness within the last year, 6) receiving no antibiotic therapy within the last 2 months, 7) having no chronic psychiatric or gastrointestinal disorder, 8) and having no non-removable metal parts in the body. Informed consent was obtained from all participants prior to joining the study. The protocol had been approved by the Ethics Board of the University of Tübingen Medical School (No. 503/2015B01, as of Aug. 26, 2015), and was registered at ClinicalTrials.gov (identifier No. NCT02793193).

2.2 Design

A randomized, double-blinded, and parallel-group design was employed. Participants were screened to exclude for the irritable bowel syndrome and psychiatric disorders using the Rome III criteria (13) and the include healthy subjects using the Patient Health Questionnaire (PHQ) (14). Demographic and baseline psychological information was also recorded. After screening, participants were randomly allocated in different intervention groups and took either probiotic or placebo for 4 weeks (28 days). The probiotic and placebo preparations in identical sachets were provided by Alimentary Health Ltd, Cork, Ireland. The randomization scheme was only unblinded after completion of the experiment and complete data evaluation. At baseline and one day after the intervention period, participants visited our lab for the MEG measurements. In addition, they visited the lab for acquiring structural MR images on a different day, regardless of their intervention schedule.

During the intervention period, participants were instructed to avoid consumption of food containing probiotics/prebiotics, or potentially immune-enhancing dietary supplements. This was supported by providing them with a list of "prohibited" foods.

2.3 Materials

Each 2 g probiotic sachet contained $1 \times 10^9$ colony-forming units *B. longum* 1714™ strain with maltodextrin and magnesium stearate; each placebo sachet contained only 2 g of maltodextrin and magnesium stearate. Participants were instructed to consume one sachet every morning with food within fifteen minutes, by mixing the content into 50 ml of water.

2.4 Questionnaires

To record participants health status, the 36-item short-form health survey (SF36) was used (15).

The SF36 includes eight subscales: physical functioning, bodily pain, role limitations due to physical health problems, role limitations due to personal or emotional problems, emotional well-being, social functioning, energy/vitality, and general health perceptions. Participants were asked to finish the SF36 at the beginning of each of the two visits.

2.5 Cyberball Game

In the CBG, the participants were asked to play a ball tossing game with two other virtual players programmed by the experimenter. They were made believe that the two players were real and were playing the game. To minimize gender effects, male participants played with 2 female players, and female participants played with 2 male players. During the game, the other players were depicted as cartoon characters with their photos aside and names below. The volunteering participant was represented by a cartoon in the middle lower part of the screen and could throw the ball to either of the other two players on the left or right, by pressing the left or right button on the response box (FIG. 2).

The CBG consisted of 4 blocks: inclusion—exclusion—inclusion—exclusion conditions; this order was maintained for all volunteers. In each inclusion block, there were 108 trials, during ⅓ (36 trials) of which the participant received the ball from the other players (for another ⅓ the ball was played to one of the other players, and for the other ⅓ between the other two players). The order of the ball throwing to the participant was pseudo-randomized. The ⅓ of trials in the inclusion block when the virtual players threw the ball to each other and not to the participant, were called "not my turn" events.

To equalize the numbers of analysed trials when the virtual players threw the ball to each other and not to the participant, we set 47 total trials in each exclusion block. The participants received the ball 3 times (trials 14, 25, or 26, and 39, 40, or 41 in block 2 and 4, respectively) to maintain their attention. The first 5 exclusion trials, the 3 trials the participant receiving the ball, and the 3 trials the participant was throwing the ball were not analysed but discarded. The remaining 36 so-called "rejection" events were used for comparison with the 36 "not my turn" events in the inclusion block. Visual stimuli of these trials did not differ in two conditions, so any difference of brain activities was supposed to be due to the participants' inner state. The trial began with the ball being presented in the cartoon for 500-2000 ms randomly to imitate a real life situation. Then the ball was moving for 2000 ms before reaching the target player (FIG. 2).

After each block of the CBG, participants needed to complete three questionnaires to assess their acute level of distress. We employed the self-report measures of the Need Threat Scale (NTS), the Mood Questionnaire (MQ) and the Subjective 'Exclusion Perception' (SEP); all these scales are validated standards for the CBG (13, 37). The NTS was designed to measure the feelings and emotional consequences of social rejection, and higher scores related to higher distress level. Its four items (rated between 1 and 5 for "weak" to "strong") comprised self-esteem, belonging, meaningful existence and control, and combined ratings have been used as a measure of social distress in previous studies. The MQ was used to assess mood, using 8 questions (are you feeling bad, good, happy, sad, pleasant, angry, friendly and unfriendly), all rated between 1 and 5. The SEP was to record participants' feeling of being included/ostracized by asking them to rate two statements ('I was ignored' and 'I was excluded') between 1 and 5.

Assessment of Need Threat Scale, Mood Questionnaire and Exclusion Perception.

All items need to be rated on a scale from 1 ('not at all') to 5 ('very much'). (R)=reversed scored.

Need

Belonging:
1. I felt disconnected with one or more players.
2. I felt rejected by other players.
3. I felt like an outsider.
4. I felt belonged to the group. (R)
5. The other players interacted with me a lot. (R)

Self-esteem:
6. I felt good about myself. (R)
7. My self-esteem was high. (R)
8. I felt I was liked. (R)
9. 1 felt insecure.
10. I felt satisfied. (R)

Meaningful existence:
11. I felt invisible.
12. I felt meaningless.
13. I felt non-existent.
14. I felt important. (R)
15. I felt useful. (R)

Control:
16. I felt powerful. (R)
17. I felt I had control over the course of the game. (R)
18. I felt I had the ability to significantly alter events. (R)
19. I felt I was unable to influence the actions of others.
20. I felt the other players decided everything.

Mood

During the game I felt:
1. Good (R)
2. Bad
3. Happy (R)
4. Sad
5. Pleasant (R)
6. Angry
7. Friendly (R)
8. Unfriendly After each of the inclusion and exclusion blocks, participants completed the NTS, the MQ, and the SEP.

2.6 Magnetoencephalography Recording

Brain magnetic fields were measured with a 275-channel whole-head magnetoencephalograph (CTF Omega, Port Coquitlam, Canada). Participants were studied in supine position. During each recording session, 5 minutes resting state was recorded prior to recording while playing the CBG. During the resting state, participants were instructed to move as little as possible and to be awake, while keeping their eyes closed. During the CBG, task instructions were projected onto a screen in front of the participants via a video projector and a mirror system. Participants were asked to fixate the screen and hold a response box to get ready for the task. Participants were also instructed to move as little as possible. MEG signals were sampled at a rate of 585.94 Hz with an anti-aliasing filter set to 292.97 Hz.

In order to overlay the brain activity derived from MEG on anatomical scans, high-resolution (1 mm, isotropic) T1-weighted structural MR images were acquired using an MPRAGE sequence with a Siemens MAGNETOM Trio 3T scanner (Siemens AG, Erlangen, Germany) (12-channel array head coil) for each participant, but at a separate occasion.

2.7 Data Analysis 2.7.1 Data Analysis: Questionnaires

Data analysis was conducted using SPSS 21 (IBM, Armonk, NY, USA). To examine whether there was a significant difference in health status between groups at baseline, scores of SF36 during the first visit were entered into a non-parametric two-independent-sample Mann-Whitney U test of Intervention as between factor (*B. longum* 1714™ vs. Placebo), as parametric assumptions of these data were violated. To test the intervention-related changes in participants' health status scored by SF36, changes from before to after the 4-weeks intervention were computed by subtracting the baseline assessment from the corresponding post-intervention values. Non-parametric two-independent-sample Mann-Whitney U test was used to examine the change of SF36 between Intervention (*B. longum* 1714™ vs. Placebo).

To examine whether subjective ratings for the CBG were different between groups at baseline, scores of NTS, MQ, and SEP acquired during the first visit were entered into an independent T-test with Intervention as between factor (*B. longum* 1714™ vs. Placebo). To control the intervention-related changes of the NTS, the MQ and SEP during the CBG, changes after each intervention were computed for each condition and entered into a 2×2 repeated measure ANOVA with Intervention as a between-factor (*B. longum* 1714™ vs. Placebo)×Condition as a within-factor (exclusion vs. inclusion). Where significant main effects or interaction were observed, pairwise post-hoc comparisons were used with a Bonferroni adjusted threshold ($\alpha=0.025$). Mean data are reported as M±SD.

2.7.2 Data Analysis: MEG—Data

Preprocessing

Analysis of the MEG data was carried out using Matlab (Mathworks, Natick, USA) and the open-source toolboxes Fieldtrip (38). The resting state dataset were cut into time windows of 2 s. Data in this time window were filtered using a 4 Hz high pass frequency filter. Non-physiological jumps in the MEG signal and trials with jump and muscle artifacts were excluded by an automatic rejection algorithm that excluded all trial in which the variance exceeded $10^{-25}$ in any channel.

The continuously recorded dataset during the CBG was segmented in epochs of 3 s with 1 s of pre-stimulus interval time-locked to the moment at which the players started to throw the ball).

Trials in which one of the virtual players threw the ball towards the other virtual player during the inclusion blocks were defined as 'inclusion' condition, and those during exclusion blocks were defined as 'exclusion' condition.

Time-Frequency Analysis

The time-frequency analysis used the multitaper windowed fast fourier transform 'MTMFFT' implemented in Fieldtrip. The 'multitaper method' (MTM) is based on Slepian sequences as tapers. The frequency of interest ranged from 4 to 30 Hz with step of 2 Hz. The frequency smoothing window is +/−3 Hz:

Source Analysis

Using the time-frequency determined by the analysis described above, oscillatory sources of theta, alpha, beta-1, beta-2 and beta-3 bands (6, 11, 16, 21, and 26 Hz) were localized using beamformer techniques. We applied the Dynamical Imaging of Coherent Sources (DICS) method. In order to estimate the individual source activity, each participant's brain recorded as T1-MR image was divided in a regular three dimensional grid with a 1 cm resolution. A spatial inverse filter was computed from both conditions and both visits, as common filter. The common filter was applied to each condition and each visit separately in order to obtain the respective source power. The MEG data in each condition were co-registered with the respective individual structural MR images respectively.

Source Statistics

We performed source-level statistics to assess effects of intervention on the data obtained from the resting-state condition and the CBG, respectively. To check if there was any difference between groups at baseline prior to any intervention, resting-state at baseline source power was compared with an independent T-test with Intervention (*B. longum* 1714™ vs. placebo) as between factor. Then, intervention-induced changes in source power were computed in each frequency band by subtracting the baseline from the post-intervention. The changes of the source power were entered into an independent T-test with Intervention (*B. longum* 1714™ vs. placebo) as between factor. For the CBG, source power at baseline in each frequency band was also tested with an independent T-test with Interventions (*B. longum* 1714™ vs. placebo) as between factor to check if brain activations showed differences between groups. Subsequently, changes in the source power after intervention were computed by subtracting the baseline values from the post-intervention for each condition in each frequency band. Changes of source power were entered in a two-way ANOVA of interventions (*B. longum* 1714™ vs. placebo)× conditions (exclusion vs. inclusion). The statistical analysis was done separately for each frequency band. To localize significant activations, the cluster-based permutation method for multiple comparisons was used with a significance level of alpha of 0.05.

Correlation Between Questionnaire and MEG Data

To investigate the relationship between changes in neural activity and changes in the subjective reports induced by *B. longum* 1714™ correlations analyses were carried out for both, the resting state recording and the CBG, respectively. For the resting state recording, averaged source power within clusters was calculated for the clusters differing significantly between both visits.

The averaged source power was correlated with changes in health status (SF36) for each group separately. For the CBG, for each condition and each intervention, source power within the clusters that differed significantly between both visits was averaged for each condition and each group. The averaged source power was correlated with changes in the scores of NTS, MQ and SEP separately for each condition and each group, using Pearson correlations.

Example 4—Effect of *B. longum* 1714™ on Energy in Healthy Subjects Using an On-Line Study 42 subjects were recruited from the general population to take part in an on-line study. Subjects were provided in a capsule format containing 1×10$^9$ colony-forming units *B. longum* 1714™. Subjects were asked to take 1 capsule per day for the duration of the study (5 weeks) and complete an on-line questionnaire on their energy, concentration and stress levels.

3 Result

A total of 40 participants were included in the analysis with half of them receiving *B. longum* 1714™ intervention. Sex of participants was matched between groups. Age and BMI of participants were not significantly different between groups (See Table 3 for details).

TABLE 3

Demographic and baseline information

| | *B. longum* 1714 ™ | Placebo | P value |
|---|---|---|---|
| Sex | | | |
| Male | N = 7 | N = 7 | n/a |
| Female | N = 13 | N = 13 | |
| Birth delivery | | | |
| Caesarean section | N = 2 | N = 2 | n/a |
| Vaginal delivery | N = 18 | N = 18 | |
| Age | 31.00 ± 2.28 | 33.00 ± 2.83 | ns. |
| BMI | 23.00 ± 0.68 | 22.00 ± 0.55 | ns. |
| SF36 | | | |
| Physical functioning | 96.84 ± 1.03 | 97.63 ± 0.80 | ns. |
| Role limitations due to physical health | 100.00 ± 0.00 | 100.00 ± 0.00 | |
| Role limitations due to emotion problems | 100.00 ± 0.00 | 95.00 ± 5.00 | |
| Energy/Vitality | 72.25 ± 2.42 | 75.25 ± 2.94 | |
| Emotional well-being | 85.78 ± 1.22 | 84.42 ± 1.75 | |
| Social functioning | 100.00 ± 0.00 | 94.74 ± 2.20 | |
| Pain | 88.75 ± 2.67 | 89.75 ± 2.80 | |
| General health | 82.50 ± 2.31 | 87.37 ± 2.40 | |
| Cyberball game NTS | | | |
| Inclusion | −28.30 ± 3.55 | −36.90 ± 2.28 | ns. |
| Exclusion | 14.33 ± 4.55 | 26.90 ± 3.48 | |
| MQ | | | |
| Inclusion | 13.80 ± 1.47 | 18.03 ± 0.99 | |
| Exclusion | 2.38 ± 2.25 | −5.48 ± 2.17 | |
| SEP | | | |
| Inclusion | −4.68 ± 0.28 | −5.30 ± 0.21 | |
| Exclusion | 0.15 ± 0.92 | 2.23 ± 0.61 | |

Abbreviations: BMI, body mass index; SF36, 36-item short-form health survey NTS, Need Threat Scale; MQ, mood questionnaire; SEP, subjective exclusion perception; ns. not significant.

3.2 MEG Data

Summaries of frequency bands and neuroanatomnical areas found to be related to *B. longum* 1714™ intervention, and associations of neural activity changes Table 4, FIG. 2 and FIG. 6 and subjective effects are provided in Table 5, FIG. 5 and FIG. 7 respectively.

TABLE 4

Summarized neuroanatomical areas and frequency bands of changed neural activities influenced by effect of condition, intervention and/or interaction of condition and intervention

| Comparison | Frequency band | Brain region | Hemisphere | P vale |
|---|---|---|---|---|
| Intervention effect on resting state: *B. longum* group vs. Placebo group | Theta ↑ | IFC | B | <0.05 |
| | | MFC | B | |
| | | SFC | B | |
| | | ACC | B | |
| | | MCC | B | |
| | Beta-3 ↓ | FFG | B | <0.05 |
| | | HIPP | B | |
| | | ITC | L | |
| | | MTC | B | |
| | | STC | L | |
| | | CBL | L | |
| Intervention effect on the Cyberball | Theta ↑ | IFC | R | 0.03 |
| | | MFC | B | |
| | | SFC | B | |

TABLE 4-continued

Summarized neuroanatomical areas and frequency bands of changed neural activities influenced by effect of condition, intervention and/or interaction of condition and intervention

| Comparison | Frequency band | Brain region | Hemisphere | P vale |
|---|---|---|---|---|
| game for all conditions: B. longum group vs. Placebo group | Alpha ↑ | ACC<br>MCC<br>SMG<br>IFC<br>MFC<br>SFC<br>ACC<br>MCC<br>SMG | L<br>B<br>R<br>R<br>B<br>B<br>B<br>B<br>R | 0.04 |

Abbreviations: IFC, inferior frontal cortex; MFC, middle frontal cortex; ACC, anterior cingulate cortex; MCC, middle cingulate cortex; FFG, fusiform gyrus; HIPP, hippocampus; ITC, inferior temporal cortex; STC, superior temporal cortex; MTC, middle temporal cortex; CBL, cerebellum; SMG, supramarginal gyrus; B, bilateral; L, left; R, right.

TABLE 5

Correlations between brain activity and mental well-being

| Groups | Subjective item | Resting state MEG | | Functional MEG during Cyberball | |
|---|---|---|---|---|---|
| | | Theta band power change | Beta-3 band power change | Theta band power change | Alpha band power change |
| Both groups | SF36-Energy/Vitality | r = 0.33<br>p = 0.04 | — | — | — |
| B. longum group | SF36-Energy/Vitality | r = 0.61<br>p = 0.007 | r = −0.50<br>p = 0.04 | r = 0.62<br>p = 0.008 | r = 0.54<br>p = 0.03 |

Abbreviations: SF36, 36-item short-form health survey; NTS, Need Threat Scale; MEG, magnetoencephalography.

Example 5—Effect of *B. longum* 1714™ on Energy in Healthy Subjects Using an On-Line Study An on-line study was performed with 42 healthy volunteers taking *B. longum* 1714™ for 5 weeks.

Participants were asked the following questions:
1. Reflecting over the last week how would you rate your Energy levels? (0=very low energy, 9=very high energy)
2. Reflecting over the last week how would you rate your ability to concentrate? (0=completely distracted, 9=excellent concentration)

The results of this study showed that energy levels and ability to concentrate increased progressively over the course of the study (FIG. 8). This supports our work which shows that *B. longum* 1714™ increases vitality/energy and reduces mental fatigue.

Recent evidence suggest that probiotics may have a role mental health and well-being (1). However, while there is increasing interest in the role of the gut in communicating with the brain, this field is in its infancy and very little is known about the effect of probiotic on mental well-being in humans. In this work, we showed that surprisingly *B. longum* 1714™ affects the brain and increased vitality and reduced mental fatigue in healthy subjects as demonstrated in 2 human studies. This is novel and not seen before. Furthermore, the *B. longum* 1714™ affected resting state brain oscillations with an increase in theta band in the frontal and cingulate cortex ($p < 0.05$) and a decrease in beta-3 band in the hippocampus, fusiform, and temporal cortex ($p < 0.05$). These areas represent in important regions of the brain such which are critical to human emotions, learning and memory functions.

*B. longum* 1714™ also affecting an individuals' neurophysiology in a way that may help in coping better with a social exclusion challenge. This is a novel finding in humans as no other probiotic has shown an impact on social ostracism. This finding was unexpected as emotional regulation is complex and it is surprising that a probiotic could impact such a complicated brain function in such a way. Previous work shows that *B. longum* 1714™ was effective in altering response to an acute stressor test (the Cold Pressor Test) when subjects were asked to perform under pressure (10). The Cold Pressor Test involves immersing your non-dominant hand into icewater until it becomes painful (usually between 1 and 2 minutes) and is a pain stimulus.

This test is designed to induce a physiological response such as elevated heart beat and cortisol levels—the 'fight or flight response'. The Cyber Ball Game works with social exclusion (ostracism) among peers, induces feelings of not being liked. It is unexpected that a probiotic would influence emotional and mental wellbeing in a model of social exclusion/ostracism.

The invention is not limited to the embodiments hereinbefore described which may be varied in detail.

REFERENCES

1. Dinan T G, Stanton C, Cryan J F. Psychobiotics: a novel class of psychotropic. Biol Psychiatry. 2013; 74(10): 720-6
2. Bravo J A, Forsythe P, Chew M V, Escaravage E, Savignac H M, Dinan T G, et al. Ingestion of *Lactobacillus* strain regulates emotional behavior and central GABA receptor expression in a mouse via the vagus nerve. Proc Natl Acad Sci USA. 2011; 108(38):16050-5.
3. Pinto-Sanchez M I, Hall G B, Ghajar K, Nardelli A, Bolino C, Lau J T, et al. Probiotic *Bifidobacterium longum* NCC3001 Reduces Depression Scores and Alters Brain Activity: A Pilot Study in Patients With Irritable Bowel Syndrome. Gastroenterology. 2017; 153(2):448-59.e8.
4. Rao A V, Bested A C, Beaulne T M, Katzman M A, Iorio C, Berardi J M, et al. A randomized, double-blind, placebo-controlled pilot study of a probiotic in emotional symptoms of chronic fatigue syndrome. Gut Pathog. 2009; 1(1):6.
5. Steenbergen L, Sellaro R, van Hemert S, Bosch J A, Colzato L S. A randomized controlled trial to test the effect of multispecies probiotics on cognitive reactivity to sad mood. Brain Behav Immun. 2015; 48:258-64.
6. Romijn A R, Rucklidge J J. Systematic review of evidence to support the theory of psychobiotics. Nutr Rev. 2015; 73(10):675-93.
7. Krieger N. Theories for social epidemiology in the 21st century: an ecosocial perspective. Int J Epidemiol. 2001; 30(4):668-77.
8. Savignac H M, Kiely B, Dinan T G, Cryan J F. Bifidobacteria exert strain-specific effects on stress-related behavior and physiology in BALB/c mice. Neurogastroenterology and motility: the official journal of the European Gastrointestinal Motility Society. 2014; 26(11): 1615-27.
9. Savignac H M, Tramullas M, Kiely B, Dinan T G, Cryan J F. Bifidobacteria modulate cognitive processes in an anxious mouse strain. Behav Brain Res. 2015; 287:59-72.

10. Allen A P, Hutch W, Borre Y E, Kennedy P J, Tenko A, Boylan G, et al. *Bifidobacterium longum* 1714 as a translational psychobiotic: modulation of stress, electrophysiology and neurocognition in healthy volunteers. Translational psychiatry. 2016; 6(11):e939.
11. Williams K D, Jarvis B. Cyberball: a program for use in research on interpersonal ostracism and acceptance. Behavior research methods. 2006; 38(1):174-80.
12. Cristofori I, Harquel S, Isnard J, Mauguiere F, Sirigu A. Monetary reward suppresses anterior insula activity during social pain. Soc Cogn Affect Neurosci. 2015; 10(12): 1668-76.
13. Longstreth G F, Thompson W G, Chey W D, Houghton L A, Mearin F, Spiller R C. Functional bowel disorders. Gastroenterology. 2006; 130(5):1480-91.
14. Kroenke K, Spitzer R L, Williams J B, Lowe B. The Patient Health Questionnaire Somatic, Anxiety, and Depressive Symptom Scales: a systematic review. General hospital psychiatry. 2010; 32(4):345-59.
15. Ware J E, Jr., Sherbourne C D. The MOS 36-item short-form health survey (SF-36). 1. Conceptual framework and item selection. Med Care. 1992; 30(6):473-83.
16. Van Schrojenstein L M, Mackus M, Otten L S, De Kruijff dD, Van de Loo A J, Kraneveld A D, Garssen J, Verster jIC, Mental resilience, perceived immune functioning, and health. J Multidiscip Healthcare. 2017 Mar. 21; 10:107-112.

What is claimed is:

1. A method of treating a subject, the method comprising administering to the subject a formulation comprising *Bifidobacterium longum* strain having the accession number NCIMB 41676 and a carrier, wherein the formulation reduces mental fatigue in the subject as measured by an increase in theta band resting state brain oscillations in the frontal and cingulate cortex or a decrease in beta-3 resting state brain oscillations in the hippocampus, fusiform, and temporal cortex.

2. The method of claim 1, wherein the formulation is administered daily.

3. The method of claim 1, wherein the formulation increases energy in the subject.

4. The method of claim 1, wherein the formulation improves vitality in the subject.

5. The method of claim 1, wherein the subject is a human.

6. The method of claim 5, wherein the subject is at least 60 years old.

7. The method of claim 5, wherein the formulation is an infant food.

8. The method of claim 1, wherein the formulation is in the form of a capsule, a tablet or a powder.

9. The method of claim 1, wherein the carrier is a food product chosen from acidified milk, a yoghurt, a frozen food a gum, a candy, a milk powder, a milk concentrate, a cheese spread, a nutritional composition, a nutritional supplement, a cereal bar, a dressing, or a beverage.

10. The method of claim 1, wherein the formulation further comprises a protein, a peptide, or both a protein and a peptide.

11. The method of claim 1, wherein the strain is present in an amount from $10^6$ cfu to $10^{10}$ cfu.

12. A method of treating a human subject, the method comprising administering to the subject a formulation *Bifidobacterium longum* strain having the accession number NCIMB 41676 and an ingestible carrier, wherein the formulation improves or sustains vitality in the subject as measured by neural activity, the 36-item short-form health survey (SF36), or both.

13. The method of claim 12, wherein the neural activity includes an increase in theta band resting state brain oscillations of the cingulate cortex or a decrease in beta-3 resting state brain oscillations in the hippocampus, fusiform, or temporal cortex.

14. The method of claim 12, wherein the formulation reduces mental fatigue in the subject.

15. The method of claim 12, wherein the formulation is in the form of a capsule, a tablet, or a powder.

16. The method of claim 12, wherein the ingestible carrier is a food product chosen from acidified milk, a yoghurt, a frozen food, a gum, a candy, a milk powder, a milk concentrate, a cheese spread, a nutritional composition, a nutritional supplement, a cereal bar, a dressing, or a beverage.

17. The method of claim 12, wherein the formulation is an infant food.

18. The method of claim 12, wherein the formulation further comprises a protein, a peptide, a lipid, a carbohydrate, a vitamin, a mineral, a trace element, or a combination thereof.

19. The method of claim 12, wherein the strain is present in an amount from $10^6$ cfu to $10^{10}$ cfu.

20. The method of claim 12, wherein the formulation is administered daily.

* * * * *

UNITED STATES PATENT AND TRADEMARK OFFICE
CERTIFICATE OF CORRECTION

| | | |
|---|---|---|
| PATENT NO. | : 12,419,920 B2 | Page 1 of 1 |
| APPLICATION NO. | : 18/455329 | |
| DATED | : September 23, 2025 | |
| INVENTOR(S) | : Eileen Frances Murphy et al. | |

It is certified that error appears in the above-identified patent and that said Letters Patent is hereby corrected as shown below:

On the Title Page

Column 2, under item (56), "Other Publications", Line 18, replace "aAnd" with -- and --.

Signed and Sealed this
Twenty-fifth Day of November, 2025

John A. Squires
*Director of the United States Patent and Trademark Office*